United States Patent [19]
Kaplan et al.

[11] Patent Number: 5,518,502
[45] Date of Patent: May 21, 1996

[54] COMPOSITIONS, METHODS AND APPARATUS FOR INHIBITING FOGGING OF ENDOSCOPE LENSES

[75] Inventors: Donald S. Kaplan, Weston; Ross R. Muth, Brookfield; Nagabhushanam Totakura; Darren E. Zinner, both of Norwalk; Corbett W. Stone, Newtown, all of Conn.

[73] Assignee: The United States Surgical Corporation, Norwalk, Conn.

[21] Appl. No.: 255,520

[22] Filed: Jun. 8, 1994

[51] Int. Cl.⁶ ............................................. A61B 1/00
[52] U.S. Cl. ........................ 600/157; 600/156; 600/169
[58] Field of Search ........................... 128/4, 6; 604/1, 604/264; 15/210.01, 214, 220.4, 244.1; 600/153, 155, 156, 157, 158, 169

[56] References Cited

U.S. PATENT DOCUMENTS

| | | |
|---|---|---|
| 2,726,962 | 12/1955 | Iorio . |
| 2,803,552 | 8/1957 | Stedman . |
| 3,048,266 | 8/1962 | Hackbel et al. . |
| 3,145,249 | 1/1963 | Meltzer . |
| 3,515,579 | 2/1969 | Shephard et al. . |
| 3,865,619 | 2/1975 | Pennewiss et al. . |
| 3,882,036 | 5/1975 | Krezanoski et al. . |
| 3,900,672 | 8/1975 | Hammond et al. . |
| 3,924,608 | 12/1975 | Mitsui . |
| 3,933,407 | 1/1976 | Tu et al. . |
| 3,935,367 | 1/1976 | Mernll et al. . |
| 3,950,289 | 4/1976 | D'Amato et al. . |
| 3,954,644 | 5/1976 | Krezanoski et al. . |
| 3,980,078 | 9/1976 | Tominaga . |
| 4,046,706 | 9/1977 | Krezanoski . |
| 4,242,412 | 12/1980 | Funaki et al. . |
| 4,281,646 | 8/1981 | Kinoshita . |
| 4,440,662 | 4/1984 | Tsuzuki et al. . |
| 4,497,550 | 2/1985 | Ouchi et al. . |
| 4,510,065 | 4/1985 | Sherman . |
| 4,543,200 | 9/1985 | Sherman . |
| 4,548,197 | 10/1985 | Kinoshita . |
| 4,613,380 | 9/1986 | Chen . |
| 4,844,052 | 7/1989 | Iwakoshi et al. . |
| 4,964,308 | 10/1990 | Edo et al. . |
| 5,022,382 | 6/1991 | Ohshoji et al. . |
| 5,125,394 | 6/1992 | Chatenerer et al. . |
| 5,133,336 | 7/1992 | Saritt et al. . |
| 5,180,760 | 1/1993 | Oshibe et al. . |
| 5,313,934 | 5/1994 | Wiita et al. . |
| 5,392,766 | 2/1995 | Masterson et al. ................ 128/4 |

FOREIGN PATENT DOCUMENTS

| | | |
|---|---|---|
| 2926921 | 2/1980 | Germany . |
| 9034048 | 7/1989 | Japan . |

*Primary Examiner*—Richard J. Apley
*Assistant Examiner*—Beverly M. Flanagan

[57] ABSTRACT

Methods for preventing and/or eliminating fogging of endoscope lenses during an endoscopic procedure which include the steps of introducing an endoscope into a body cavity and contacting the endoscope lens with a biocompatible and biodegradable composition containing a polyalkylene oxide while the lens is positioned within the body. Alternatively, the endoscope may be coated with a biocompatible polyHEMA coating which is activated by a biocompatible solution, such as water or saline, which may be introduced during use through a fluid conduit on the endoscope. Devices for preventing and/or eliminating fogging of endoscope lenses during endoscopic procedures and conveying antifogging solutions to the distal end of the endoscope are also provided, and may include a distensible applicator.

22 Claims, 9 Drawing Sheets

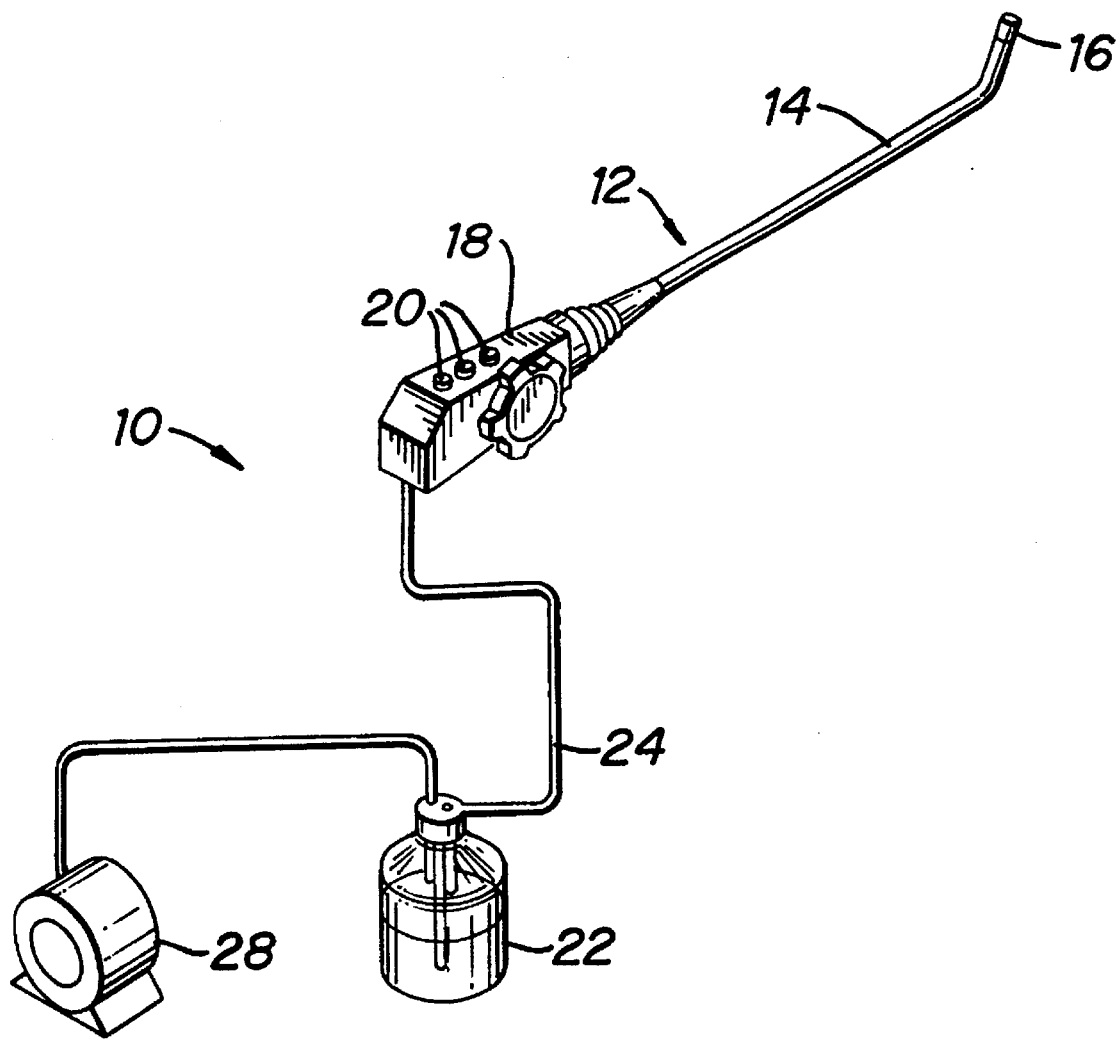
FIG_1

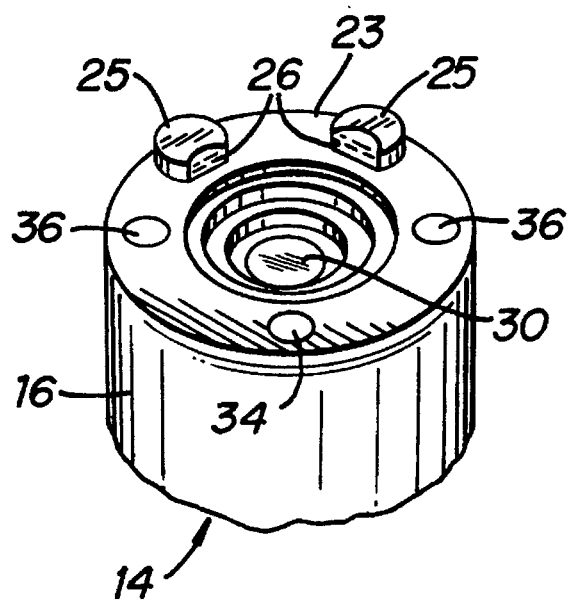
FIG_2
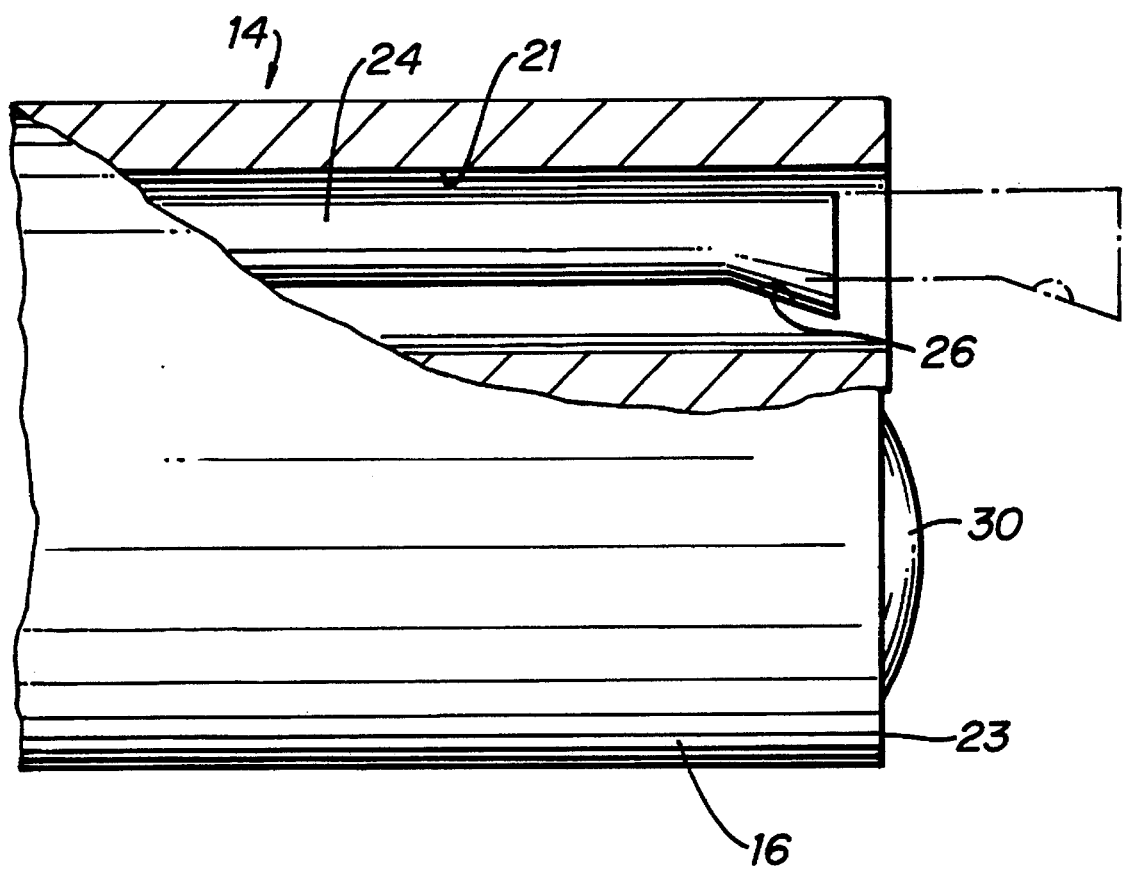
FIG_3

COMPOSITIONS, METHODS AND APPARATUS FOR INHIBITING FOGGING OF ENDOSCOPE LENSES

BACKGROUND OF THE INVENTION

1. Technical Field

This invention relates to the reduction of fogging of medical device lenses. More particularly, compositions and methods for reducing and inhibiting fogging of endoscope lenses are disclosed.

2. Description of Related Art

It is desirable to eliminate the formation of fog or moisture on transparent or reflecting surfaces such as glass and plastic materials. This is particularly true for medical instrument lenses used during diagnostic and surgical procedures. Endoscopes provide medical diagnosis and treatment at relatively inaccessible and remote locations within a body. Endoscope lenses are prone to fogging due to ambient temperature changes. When an endoscope is inserted into a human body, fog or fine water droplets adhere to the lens due to the cooling of water vapor in the body cavity when the endoscope having a temperature of the ambient atmosphere is introduced to the body cavity having a higher temperature of about 36° C. and 100% humidity.

During an endoscopic procedure, the temperature of the lens gradually increases to the temperature of the body cavity. However, it is sometimes necessary to supply water or air to the body cavity. The addition of water or air to the body cavity lowers the temperature of the endoscope lens which also contributes to fogging of the lens.

Fogging of the endoscope lens obstructs the endoscope operator's view. The view through the endoscope lens generally becomes blurred or "smokey" due to the fogging. Consequently, the length of time required for completing endoscopic procedures is greatly increased. This is extremely disadvantageous for both the operator and the patient undergoing the endoscopic procedure. Furthermore, fogging of endoscopic lenses interferes with endoscopic photography and video endoscopy.

Certain attempts have been made to reduce or eliminate fogging of transparent or reflecting surfaces such as glass, lenses, contact lenses, eyeglasses, goggles, diving masks, mirrors, and plastic food wrapping material. A number of antifogging polymeric coatings, films, and solutions are known in the art, including acrylate-based polymers (see, for example, U.S. Pat. Nos. 3,515,579, 3,865,619 and 3,900,672) and organosiloxane-oxyalkylene block copolymers (see U.S. Pat. No. 3,933,407). Other antifogging compositions include polyethoxy alcohol, polyoxyethylene sorbitan monostearate, polyoxyethylene sorbitan monooleate, polyoxyethylene esters or ethers, polymeric vinyl films, polyvinyl alcohol, polyalkylene imine polymer and block copolymers of polyurethane and hydrophilic copolyacrylics. (See U.S. Pat. Nos. 2,803,552, 2,726,962, 3,048,266, 4,964,308, 3,935,367, 3,950,289, 4,242,412 and 5,180,760.)

Certain apparatuses and methods specifically designed for cleaning endoscope lenses are also known in the art. Modifications to endoscopic instruments such as endoscopic lens wiper devices and lens adapters have been employed for eliminating materials and fog from lenses. (See U.S. Pat. Nos. 3,145,249 and 5,125,394.) Other methods include the application of air having the same temperature as the ambient atmosphere over the surface of an endoscope lens to stabilize the temperature of the lens while it is inside a body. (See U.S. Pat. No. 4,497,500.) U.S. Pat. No. 3,924,608 describes an endoscope having a suction port for removing liquid from the outer surface of the distal endoscope observation lens.

Many prior methods for eliminating fog or other materials from endoscope lenses are time consuming and increase the risk of infection because they require removal of the endoscope from the body. In these methods, once fog develops on the endoscope lens, the endoscope is removed from the body cavity, and antifogging compositions are applied to the lens with a sponge. A dry sponge is then used to wipe away any unevaporated composition from the endoscope lens. The endoscope is then reinserted into the body to continue the procedure. Methods for cleaning endoscopic lenses by applying liquid or gas directly to the endoscope lens during an endoscopic procedure overcome the drawbacks of methods which require removal of the endoscope from a body to clean it. A liquid or gas is delivered through an outlet or nozzle at the distal end of the endoscope during the endoscopic procedure. (See U.S. Pat. Nos. 3,980,078, 4,281,646, 4,844,052, 4,548,197 5,022,382 and 5,133,336.) However, where liquid is applied to an endoscopic lens during a procedure it is often necessary to vigorously remove nonbiocompatible liquids from the body cavity by aspiration in order to avoid adverse side effects.

While polyoxyalkylenes have been used as a component in solutions designed for cleaning and wetting contact lenses (see U.S. Pat. Nos. 3,954,644, 3,882,036, 4,046,706, 4,440,662, 4,510,065, 4,543,200 and 4,613,380), polyoxyalkylene solutions have not been used to reduce or eliminate fog on endoscope lenses while the endoscope remains within the body.

An efficient and safe method for eliminating fog from endoscope lenses during endoscopic procedures which does not require removal of the endoscope from the body cavity and which employs only biocompatible materials would be desirable.

SUMMARY

Compositions, devices and methods for eliminating fogging of an endoscope lens during an endoscopic procedure by contacting the endoscope lens with a biocompatible and biodegradable composition while the lens is positioned within a body are provided. In a preferred embodiment of the subject invention, a method is provided which comprises introducing a distal end portion of an endoscope to a surgical site and contacting a lens associated with the distal end portion of the endoscope with the antifogging composition. The lens can be coated with a composition containing polyhydroxyethyl methacrylate prior to insertion into the body and application of the anti-fogging composition. The preferred antifogging composition comprises a polyoxyalkylene solution. The most preferred polyoxyalkylene is a polyoxypropylene-polyoxyethylene block copolymer. The devices or surgical apparatuses include an elongated insertion member having at least one lens disposed at the distal end thereof. Means for selectively directing a quantity of fluid to the endoscope lens while the endoscope is positioned within a body cavity or at a surgical site is provided. A particularly useful means for selectively directing a quantity of fluid to the lens is a distensible applicator movable from a first, retracted position to a second, extended position in response to fluid pressure.

BRIEF DESCRIPTION OF THE DRAWINGS

FIG. 1 is a perspective view of an exemplary endoscopic apparatus;

FIG. 2 is a perspective view of an end portion of the endoscope of FIG. 1;

FIG. 3 is side elevation view in partial cross-section of an alternative embodiment for the end portion of the endoscope of FIG. 1, illustrating means for applying the antifogging composition to an endoscope observation lens system;

DETAILED DESCRIPTION

Figure 4A:
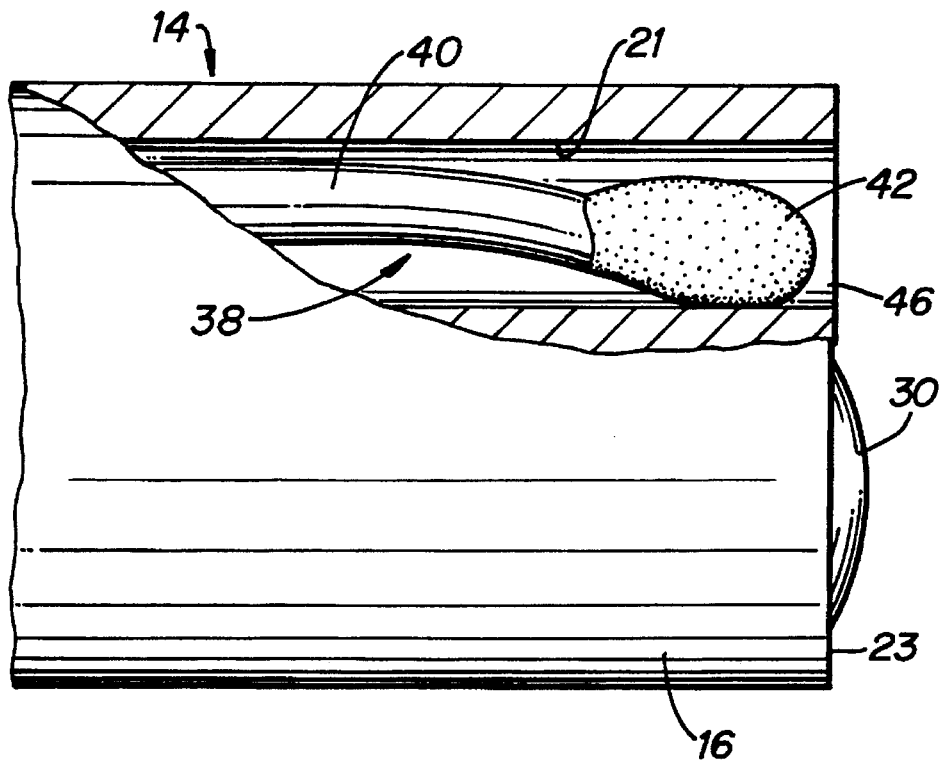
FIGS. 4A and 4B are side elevational views in partial cross-section of another alternative embodiment of the end portion of the endoscope of FIG. 1, illustrating swabbing means for applying the antifogging composition to an endoscope observation lens system.

A convenient and efficient method for eliminating the formation of fog on endoscope lenses is provided. The term "endoscope" as used herein means any device inserted into a body having a lens for viewing the interior of the body and viewing means located outside the body. The endoscopic image may be viewed with the eye, either directly or via television or video. The antifogging composition may be used on all types of endoscopes such as gastroscopes, laparoscopes and arthroscopes.

The present method overcomes the drawbacks of prior methods known in the art. The antifogging composition is biocompatible and biodegradable. Therefore, the composition may be delivered to an endoscope lens during an endoscopic procedure without removing the endoscope from the body cavity. Thus, the time it takes to perform endoscopic procedures is reduced. Elimination of fogging of the endoscope lens provides the optical clarity that is necessary for the endoscope operator to perform endoscopic procedures. The risk of infection is also greatly reduced because the endoscope is not removed from the body cavity during a procedure. In addition, the antifogging solution is also useful for removing blood, mucopolysaccharides, and lipids from the endoscope lens.

The antifogging solutions contain polyoxyalkylenes. Polyoxyalkylenes are hydrophilic polymers which readily form aqueous solutions. Suitable polyoxyalkylenes include polymers such as polyoxyethylene, polyoxypropylene and copolymers or blends thereof. Biocompatible polyoxyalkylenes are employed so that once applied to the lens they need not be vigorously removed from the body cavity. Particularly useful polyoxyalkylenes for use with this invention are products sold under the tradename "PLURONIC" by BASF Corporation.

PLURONIC products are polyoxypropylene-polyoxyethylene block copolymers. These copolymers are formed by condensation of propylene oxide onto a propylene glycol nucleus followed by the condensation of ethylene oxide onto both ends of the polyoxypropylene base. Examples of particularly useful commercially available copolymers that may be used with this invention are those PLURONIC products having the designations F-38, L-44, L-62, L-64, P-75, P-65, F-77, F-88, F-98 and F-108. These PLURONIC products have a molecular weight between about 1,900 and 15,500 and a solubility in water of greater than 10%. The most preferred PLURONIC products are F-68 and F-127, which have molecular weights of about 8,400 and 12,600, respectively. In the most preferred embodiment, the polyalkylene oxide is applied to the lens as a solution in a biocompatible solvent. The polyoxyalkylene should constitute from about 0.001 to about 10 percent by weight of the solution. Preferably, the polyoxyalkylene is present in the solution in an amount from 0.01 to 5 weight percent.

Thus, for example, one of the above-mentioned PLURONIC products may be applied to the endoscope lens in an aqueous solution of from about 0.01 to 5 weight percent. The solution may be formed using distilled or non-distilled water. Alternatively, a biocompatible buffered solution having a pH of 7, such as saline, may be used as the solvent.

Devices and methods for transmitting liquid or gas through an endoscope to the observation lens at the distal end of the endoscope are known. See U.S. Pat. Nos. 4,281,646, 4,497,550, 4,548,197, 4,844,052, 5,022,382, 5,207,213 and 5,133,336 the disclosures of which are hereby incorporated by reference. Any device or method may be used to apply the antifogging composition to an endoscope observation lens system, provided that the method does not require removal of the endoscope from the body. For example, the composition may be swabbed, sprayed, brushed or coated onto the lens. The composition may also be applied with a sponge, swab or other suitable material without removing the endoscope from the body. The antifogging composition may be directly applied to the lens in situ by spraying the solution through an outlet or outlets located at the distal end portion of the elongated insertion member. For example, the outlet may have a plurality of apertures for directing a spray of the antifogging composition or the outlet may be a liquid transmitting nozzle disposed at the distal end of the insertion member for directing the antifogging composition in a dispersed pattern.

The antifogging composition is applied during an endoscopic procedure to an endoscope lens at the distal end of an endoscope insertion member. The term distal refers to the end of the apparatus which is furthest from the operator. The composition may be applied to any suitable endoscope lens material such as glass, plastic, metal, or other translucent solid. The most preferred endoscope lens for use with the invention is an acrylic lens.

FIG. 1 depicts the surgical apparatus 10 for use with this invention which includes an endoscope 12 having an elongated insertion member 14 which is inserted into a body during an endoscopic procedure. The insertion member 14 may be either rigid or flexible depending on the procedure being performed. The distal end portion 16 of the endoscope insertion member 14 includes an objective lens 30 (see FIG.

2) for viewing the interior of the body. Body portion 18 includes controls for aspiration, gas insufflation and liquid instillation operations. Operating buttons 20 on the body portion are used to activate the various operations. It is also contemplated that rather than buttons 20, the activation means may have a trigger, trumpet valve or other configuration.

Furthermore, the endoscope includes a reservoir means, tank 22, for holding the antifogging composition. It is also contemplated that the reservoir means may be disposed within the body portion 18 or insertion portion 14 of the endoscope (as seen in FIGS. 4A) rather than being located remote from the endoscopic device. Conduit means 24 delivers the composition from the reservoir means to the distal end portion of the insertion member. Means for spraying (or otherwise applying) the antifogging composition through outlet means such as aperture 26 onto the observation lens may be provided. Means for transporting the antifogging solution from the reservoir to the outlet means, such as pump 28 actually causes movement of the solution into contact with the lens. It is also contemplated that a canister of compressed gas (e.g. air) can be disposed within the body of the endoscope to move the solution from the reservoir to the lens. Other means contemplated for transporting the solution from the reservoir to the outlet include a syringe or plunger mechanism.

FIG. 2 depicts a distal end portion 16 of the endoscope insertion member 14. An observation lens 30 is located on distal end portion 16 and may be recessed, flush with or extended beyond the distalmost surface 23 of the insertion portion 14. In this particular embodiment, the antifogging solution is delivered to the lens via nozzle 25 which is fixedly located on the distalmost surface 23 of the insertion member. Aperture 26 is located on nozzle 25 above the observation lens 30 for spraying the antifogging composition onto the observation lens. It should be understood that the location of the outlet means is not limited to this particular position. Pump 28 forces the solution through conduit 24 to the aperture 26 at the distal end of the endoscope insertion member. The insertion member may also have one or more inlets 34 for aspiration of gas and/or liquid. The endoscope may also be equipped with an illumination system 36, such as a fiber optic bundle, which illuminates the area being imaged.

FIG. 3 schematically depicts a longitudinal partial cross-sectional view of the distal end portion 16 of an endoscope insertion member 14. In this particular embodiment, the distal end of the insertion member includes a retractable means for spraying the antifogging composition through the aperture 26 onto the observation lens. The aperture 26 may be located on a separate nozzle mounted to conduit 24 or may be integrally formed on the conduit as shown in FIG. 3. In this embodiment, conduit 24 is located within channel 21 in a manner such that aperture 26 can be extended beyond the distalmost face 23 of the endoscope and beyond objective lens 30 so that the antifogging composition may be sprayed onto and/or across the objective lens. In FIG. 3, the extended position is shown in phantom lines.

Figure 4B:
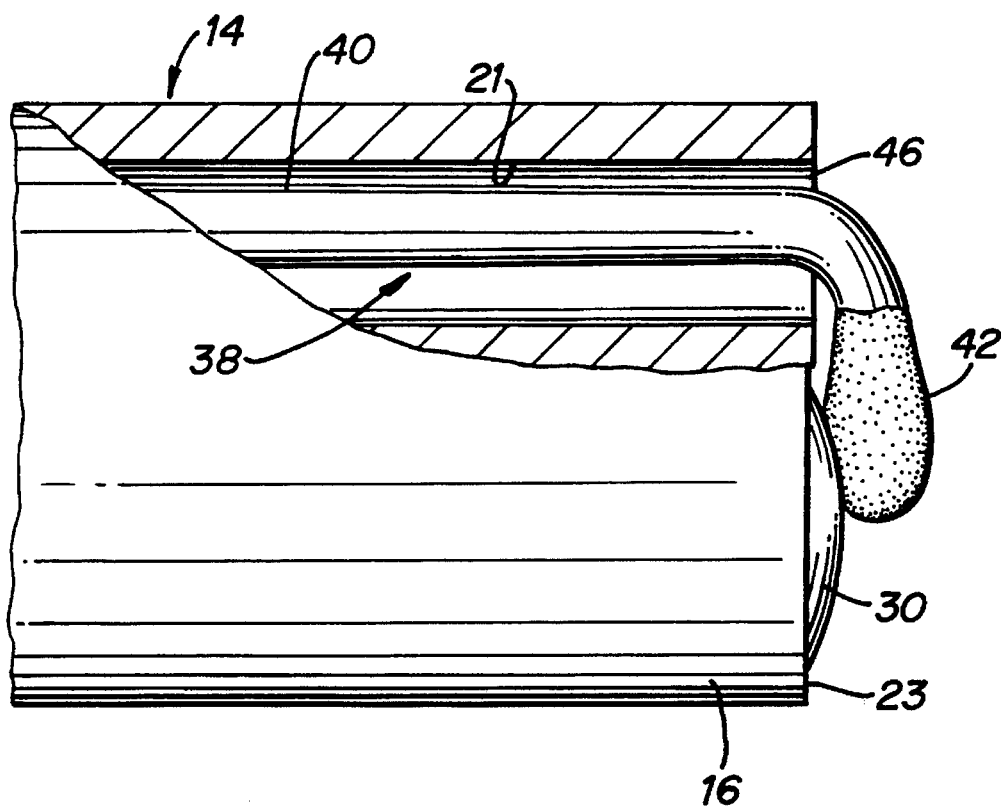

FIGS. 4A and 4B schematically depict a longitudinal partial cross-sectional view of an alternative embodiment for applying the antifogging composition. A swabbing means 38 has an elongated shaft 40 made at least in part from an elastic or resilient material and an absorbent material 42 at the distal end. In this embodiment, absorbent material 42, which is saturated with the antifogging solution, serves as the reservoir means and shaft 40, which causes the swab to move into contact with the lens, serves as the means for transporting the antifogging solution. The term "elastic material" means a material that has spring-like properties, which is capable of being deformed by an applied stress and then springing back, or recovering, to its original unstressed shape or configuration when the stress is removed. The elastic material is preferably superelastic. The elastic material may be polymeric or metallic, or a combination of both. Such materials include silicone, polyvinyl resins, polyethylene, resilient polyacetals, polyurethane, synthetic rubbers, "Teflon" (tetrafluoroethylene fluorocarbon polymer), spring tempered steel, and spring tempered stainless steel.

The use of shape memory alloys is preferred. Shape memory alloys that exhibit superelasticity are especially preferred. An example of a shape memory alloy suitable for this application is "TINEL" brand material which is available from Raythem Corporation of Menlo Park, Calif. This material is comprised of a composition of nickel and titanium which can be formed into a structural element the configuration of which can be controlled mechanically by application of external stress or thermally by the application of heat.

The swabbing means 38 is positioned within a tube channel 21 in the endoscope insertion member. FIG. 4A depicts the swabbing means 38 in a deformed stressed configuration wherein the elongated shaft 40 and absorbent material 42 are disposed within the tube channel 21. The absorbent material may be a porous, sponge-like material or a textile material (e.g., knitted, woven, non-woven, etc.). FIG. 4B depicts the swabbing means 38 in a preformed unstressed configuration extending from the tube channel outlet 46 located at the distal end of the insertion member 14. Any known means may be employed to effectuate extension of the swab out of the insertion member. Upon movement out of the insertion member, the distal end of swabbing means 38 assumes an arcuate preformed unstressed configuration which allows the absorbent material 42 to contact the endoscope observation lens 30 thereby providing a means for applying the antifogging solution to the observation lens 30. Preferably, the arcuate formation of the elongated shaft is a 90° curvature. While a single pass of the absorbent material 42 across the lens may be sufficient to apply an adequate mount of the antifogging material onto the lens, it is also contemplated that a series of passes could be made. It is also contemplated that a conduit may extend through shaft 40 to replenish the supply of antifogging solution to absorbent material 42.

Figures 5, 6:
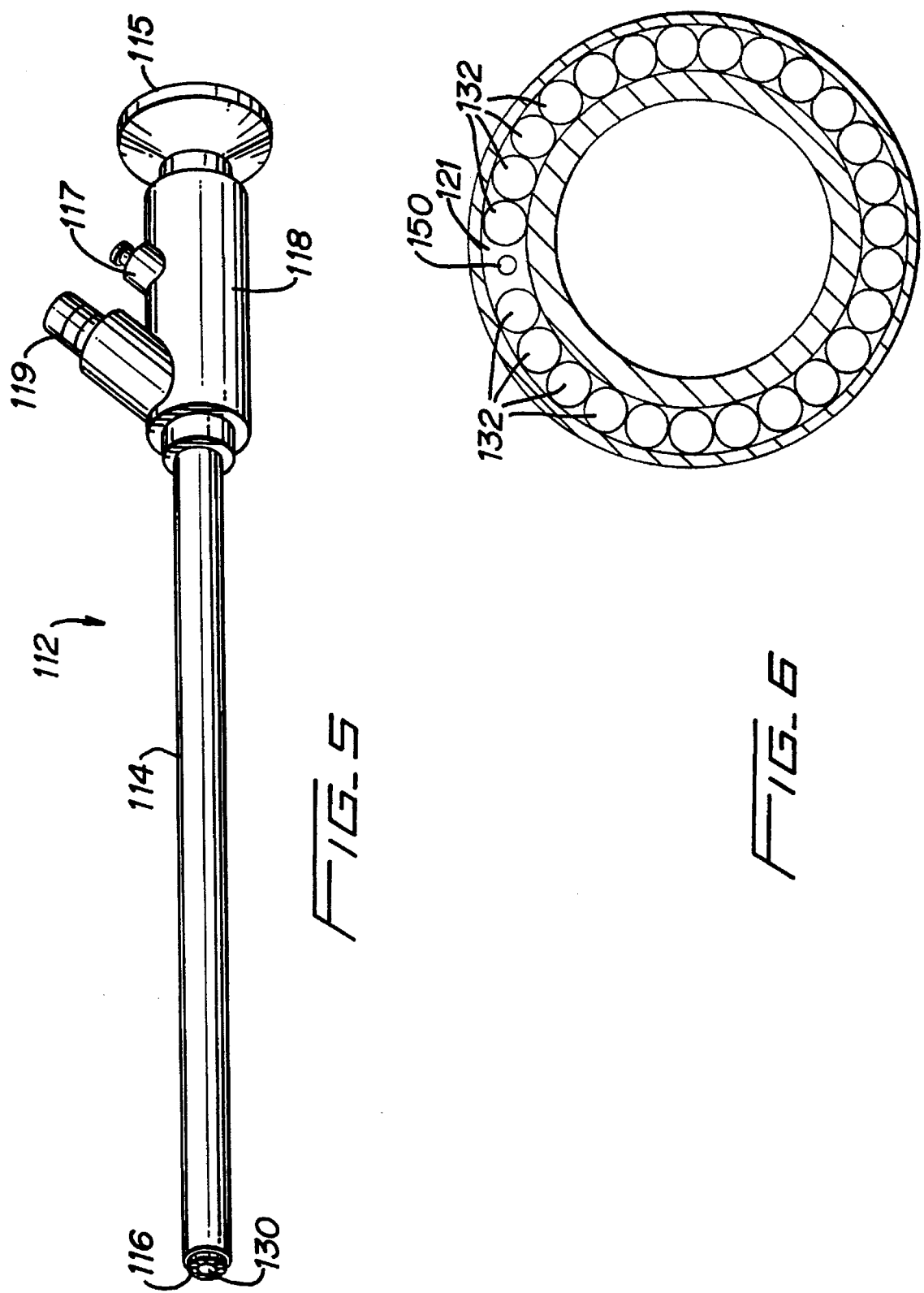
FIG. 5 is a perspective view of another embodiment of an endoscope.
FIG. 6 is a front plan view of the distal end of the endoscope of FIG. 5.

FIGS. 5, 6, 7A and 7B illustrate an alternative embodiment of an endoscopic instrument. FIG. 5 depicts an endoscope 112 having an elongated insertion member 114. Distal end portion 116 of insertion member 114 includes a lens 130. Body portion 118 of endoscope 112 includes viewing means 115 at its proximal end for observing the interior of a body cavity and access means 119 for supplying a solution to be applied to lens 130. Access means 119 can be, for example, a Luer connector and Luer or any other type of valve.

As best seen in FIG. 6, lens 130 is substantially surrounded by optic fibers 132 which transmit light to the distal end portion 116 of endoscope 112, thereby illuminating the endoscope's field of view. Optic fibers 132 extend substantially parallel through the elongated insertion member 114 to the body portion 118. A light source (not shown) attached to connector 117 provides light energy which is transmitted to the field of view via optic fibers 132.

A conduit 124 communicates with access means 119 and extends through elongated insertion member 114 between two of the optic fibers 132. Conduit 124 ends proximal the distal end 116 of the insertion member 114, thereby forming a space 121 between the optic fibers 132 at the distal end 116 of the insertion member 114.

A distensible applicator such as flexible bladder 150 is positioned on the distal end of conduit 124. Bladder 150 is thus located in space 121. Bladder 150 can be made from any expandable, elastic material such as, for example, latex rubber. In its uninflated state, bladder 150 is located completely within the elongated insertion member 114. Aperture means, e.g., slot 126, is formed in bladder 150.

Figure 7A:
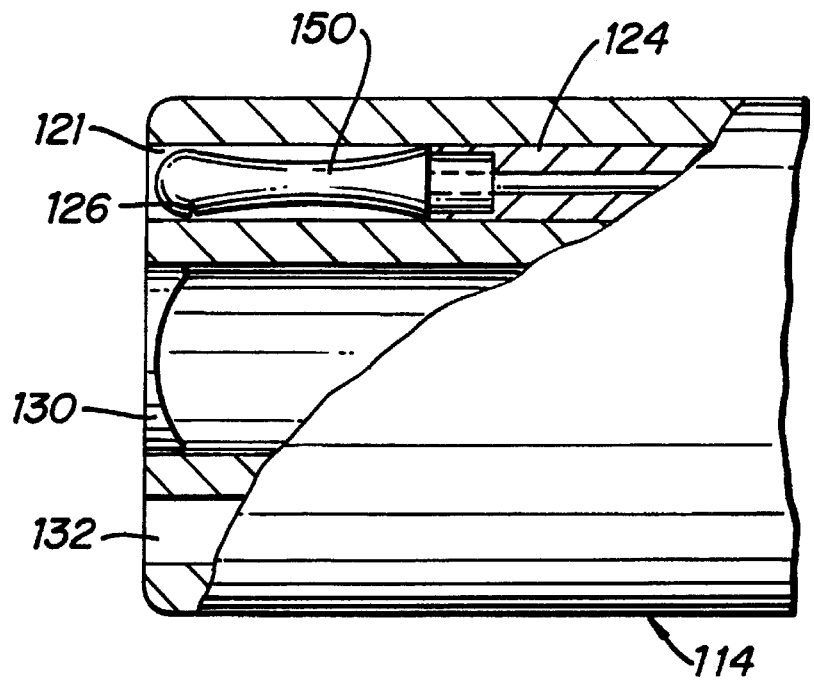
FIG. 7A and 7B are side elevational views in partial cross-section of the distal end of the endoscope of FIG. 5, illustrating a distensible applicator in retracted and extended positions.
Figure 7B:
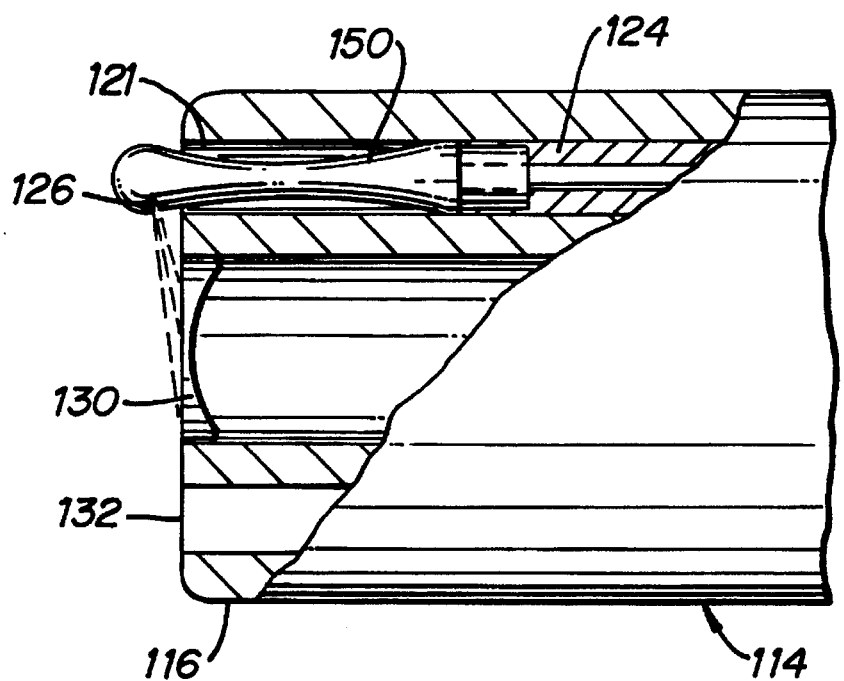

When fluid is provided through access means 119, it flows through conduit 124, filling and inflating bladder 150. Any known means may be employed to provide fluid through access means 119. For example, a syringe structure (not shown) which provides both fluid transporting means (plunger) and reservoir means (fluid chamber) can be employed to provide fluid via access means 119. As bladder 150 fills with fluid, pressure builds within bladder 150 causing it to expand and move to its extended position, with slot 126 positioned beyond distal end 116 of insertion member 114. Pressure from the fluid causes slot 126 to open, thereby providing an opening for spraying fluid onto the outer surface of lens 130 as shown in FIG. 7B. When a flow of fluid is no longer being supplied to conduit 124, the elastic nature of bladder 150 causes it to contract, deflate and withdraw back into the insertion member 114. Upon the cessation of pressure provided by the flow of fluid and the resulting deflation of bladder 150, slot 126 closes, thereby preventing the leakage of residual fluid which may be contained within the bladder 150 or conduit 124.

Figure 8:
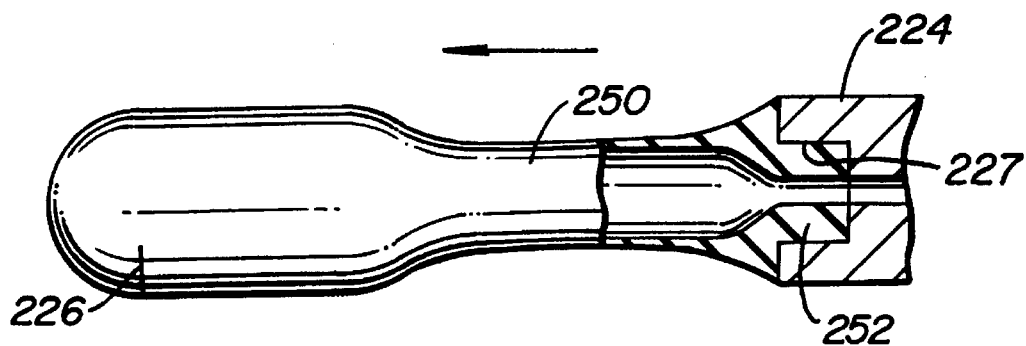
FIG. 8 is a side elevational view in partial cross-section of an alternative embodiment of applicator means.
Figure 9:
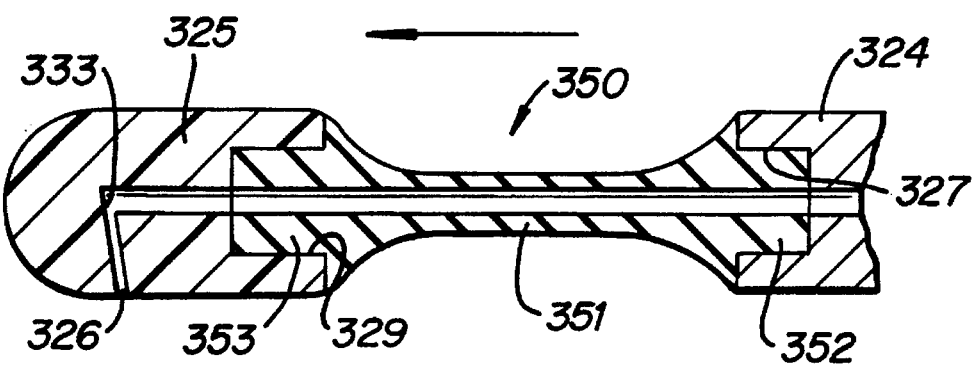
FIG. 9 is a side elevational view in partial cross-section of another alternative embodiment of applicator means.
Figure 10:
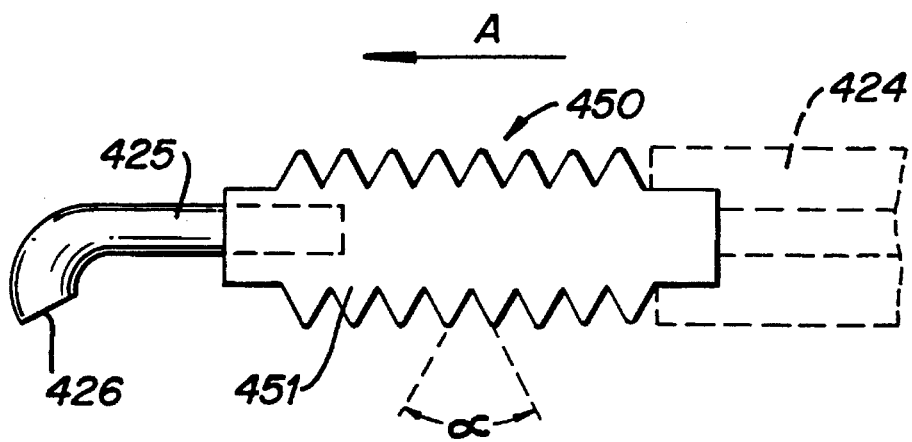
FIG. 10 is a side elevational view of another alternative embodiment of applicator means.

FIGS. 8–10 show other applicators which may be used in this invention. As seen in FIG. 8, a distensible applicator may include latex rubber bladder 250 having slot 226 formed therein and a cylindrical portion 252 formed at the proximal end thereof. Bladder 250 is mounted to conduit 224 by inserting cylindrical portion 252 of bladder 250 into opening 227 formed in the distal end of conduit 224. Other than the way bladder 250 is mounted to conduit 224, this distensible applicator operates in the same manner as bladder 150.

Referring now to FIG. 9, another applicator, generally denoted by the numeral 350 includes a nozzle 325 and a latex rubber connector 351. Connector 351 joins nozzle 325 to conduit 324. The connector has a cylindrical proximal end 352 which is inserted into opening 327 formed in the distal end of conduit 324, and a cylindrical distal end 353 which is inserted into opening 329 formed in the proximal end of nozzle 325. Fluid provided through conduit 324 passes through connector 351 and into nozzle 325. As the fluid turns to exit nozzle 325 through aperture 326, the fluid applies pressure against wall 333. Connector 351 stretches in response to this pressure, causing nozzle 325 to extend out of the distal end of the endoscope such that fluid leaving aperture 326 sprays onto the lens of the endoscope. When the flow of fluid through conduit 324 ceases, pressure against wall 333 also ceases and connector 351 (due to the elastic nature of material of construction) retracts to its original position thereby retracting nozzle 325 back into the endoscope.

Turning now to FIG. 10, applicator 450 includes nozzle 425 and an accordion-like latex rubber connector 451. The proximal end 452 of connector 451 is attached to conduit 424 as in the previous embodiment. The proximal end of nozzle 425 is inserted into the distal end of connector 451 as shown in FIG. 10. The distal end of nozzle 425 includes an aperture 426 and is shaped to direct fluid passing through aperture 426 onto the lens of the endoscope. The operation of the embodiment of FIG. 10 is similar to that of the previous embodiment. Specifically, fluid provided through conduit 424 passes through connector 451 and into nozzle 425. As the fluid turns to exit nozzle 425 through aperture 426, the fluid applies pressure against the nozzle 425 which causes connector 451 to stretch. As connector 451 stretches, angle a increases and nozzle 425 extends out of the distal end of the endoscope. Fluid exiting aperture 426 is thus directed onto the lens of the endoscope. When the flow of fluid through conduit 424 ceases, connector 451 retracts to its original position, thereby retracting nozzle 425 back into the endoscope.

Figure 11:
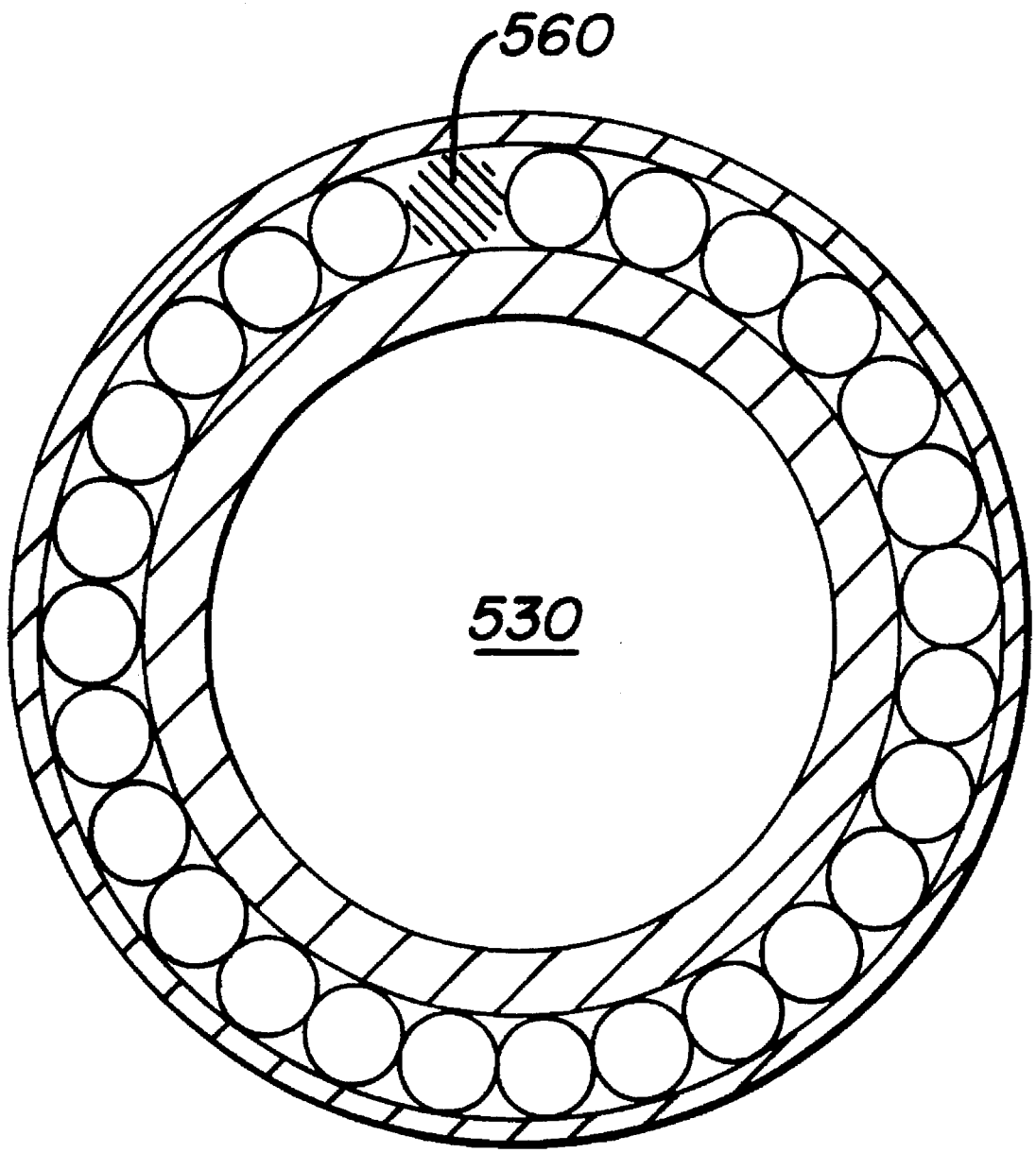
FIG. 11 is a front plan view of another embodiment of an endoscope.
Figure 12A:
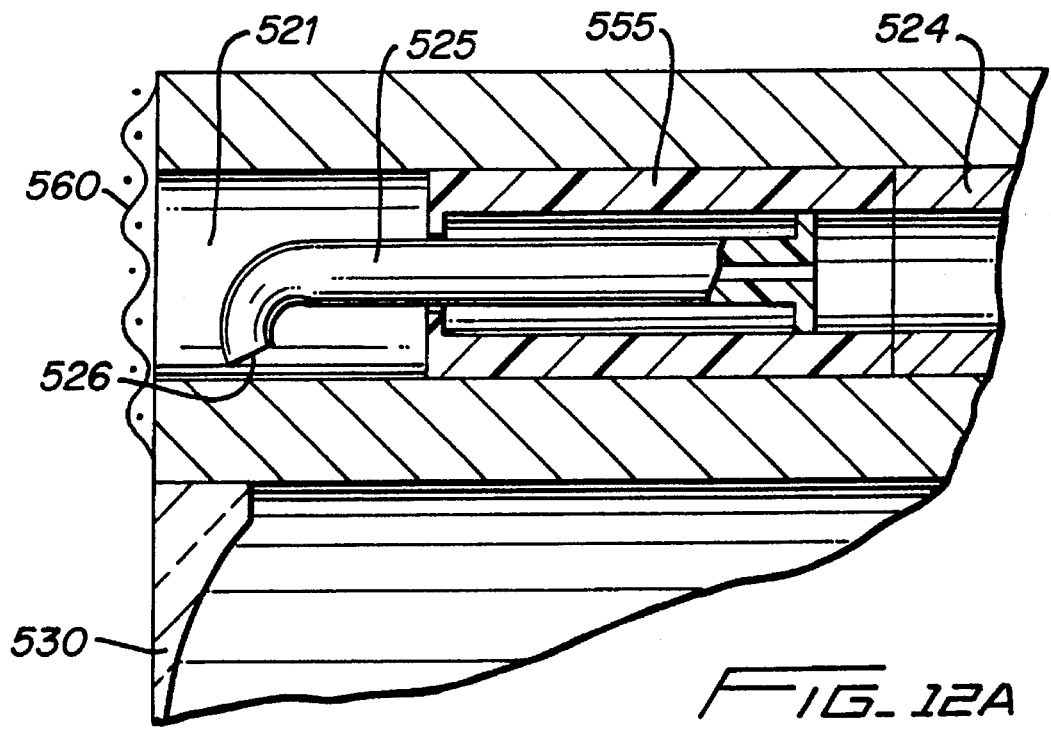
FIG. 12A and 12B are partial side elevational views in partial cross-section of the end portion of the endoscope of FIG. 11, illustrating the applicator in retracted and extended positions.
Figure 12B:
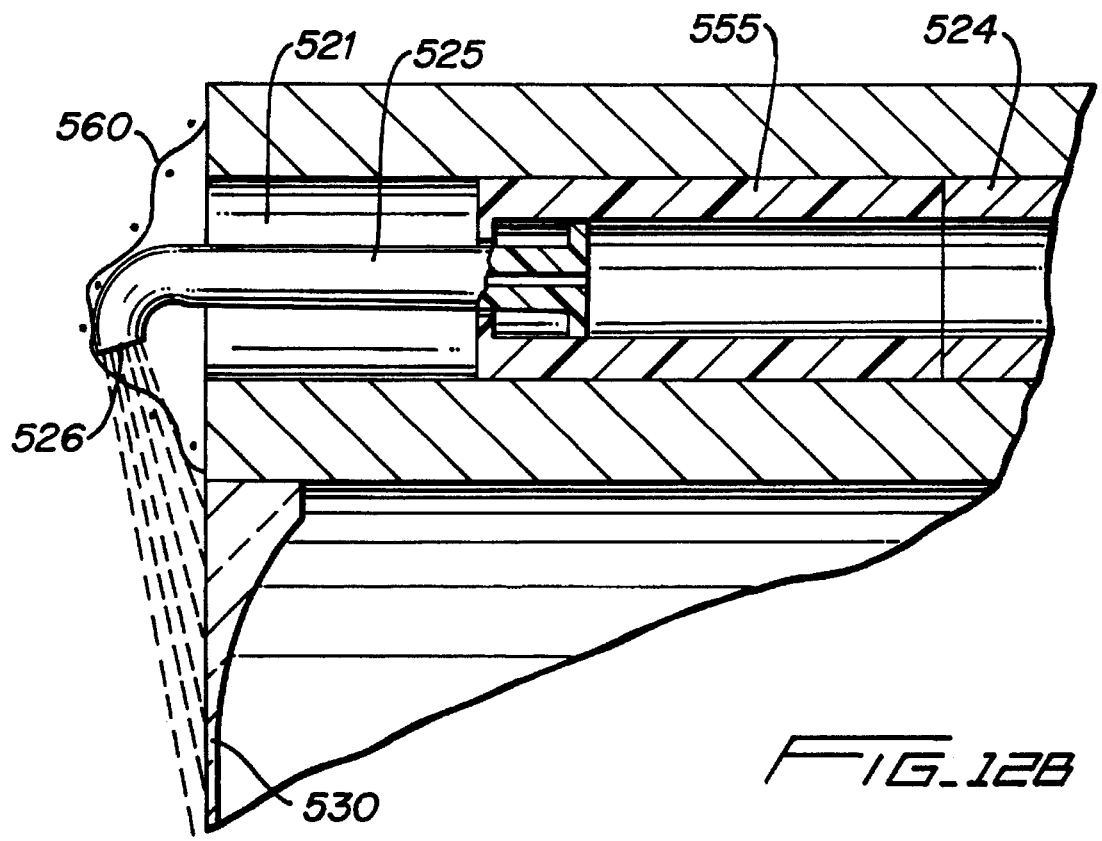

Another retractable endoscope sprayer is shown in FIGS. 11, 12A and 12B. While fluid pressure extends the nozzle 525 in this embodiment, the nozzle 525 is retracted by contact with an elastic mesh 560 which is attached to the distal end of the endoscope covering space 521. As best seen in FIG. 12A, nozzle 525 is slidably positioned within sleeve 555 and both pieces are positioned within space 521 as shown. The distal end of nozzle 525 includes aperture 526 and is shaped to direct fluid passing through aperture 526 onto the lens of the endoscope. Fluid provided through conduit 524 passes into sleeve 555 and into nozzle 525. As the fluid turns to exit nozzle 525 through aperture 526, the fluid applies pressure against the nozzle 526, causing it to slide distally within sleeve 555. As nozzle 525 slides beyond the distal end of the endoscope, it pushes against and stretches elastic mesh 560. Fluid exiting aperture 526 passes through the stretched mesh 560 and onto lens 530 as best seen in FIG. 12B. When the flow of fluid through conduit 524 ceases, nozzle 525 no longer exerts pressure against mesh 560 which, due to its elastic nature, slides nozzle 525 distally back into space 521.

It should be understood that any type of fluid may be applied to an endoscope lens using the embodiments shown in FIGS. 5 through 12B. Accordingly, the antifogging solution previously described, or any other biocompatible liquid or gas may be applied to the lens to clean or inhibit fogging. Where a fluid other than the previously described antifogging solution is applied to lens 130, the lens may advantageously be coated with an antifogging coating. Thus, it is contemplated that an antifogging coating may be applied to the lens of the endoscope prior to use, such as during manufacture of the endoscope or shortly before use, which is activated by application of a solution before or during use.

One suitable antifogging coating includes polyhydroxy ethyl methacrylate (polyHEMA). The antifogging coating can be applied to lens 130 by dipping the lens, either before or after assembly of the endoscope, in a solution of polyHEMA in a suitable solvent and allowed to dry. Useful solvents will be sufficiently volatile to dry in a reasonable length of time, and will not leave any toxic residue on the lens. Ethanol is a particularly preferred solvent. The solution used to coat the lens can contain from about 0.1 to about 25 percent polyHEMA by weight. Preferably, the solution contains from about 1 to about 5 percent polyHEMA by weight, and most preferably about 2 to about 3 percent polyHEMA by weight. PolyHEMA coatings inhibit fogging, particularly when accompanied by the application of a spray of saline solution or water onto the lens prior to or during use, without interfering substantially with the clarity of the field of view.

Advantageously, the polyHEMA coating may be applied prior to sterilizing the endoscope. Thus, the polyHEMA coating may be applied to the distal lens surface during manufacture of the endoscope, with the endoscope thereafter packaged and sterilized (such as by ethylene oxide sterilization) to supply a sterile endoscope having a polyHEMA coating on the distal lens surface. In use, operating room personnel remove the sterile endoscope for use and, optionally, apply activating solution (such as water or saline solution) to the distal lens surface prior to insertion of the endoscope into the body. Alternatively, where a fluid conduit is provided as part of the endoscope, the endoscope may be inserted into the body directly into the body upon removal from the package, thereafter applying solution as required to clear the endoscope during use. A particular advantage of the polyHEMA coating is that the antifogging solution may be water or saline solution, which are inert.

Figure 13:
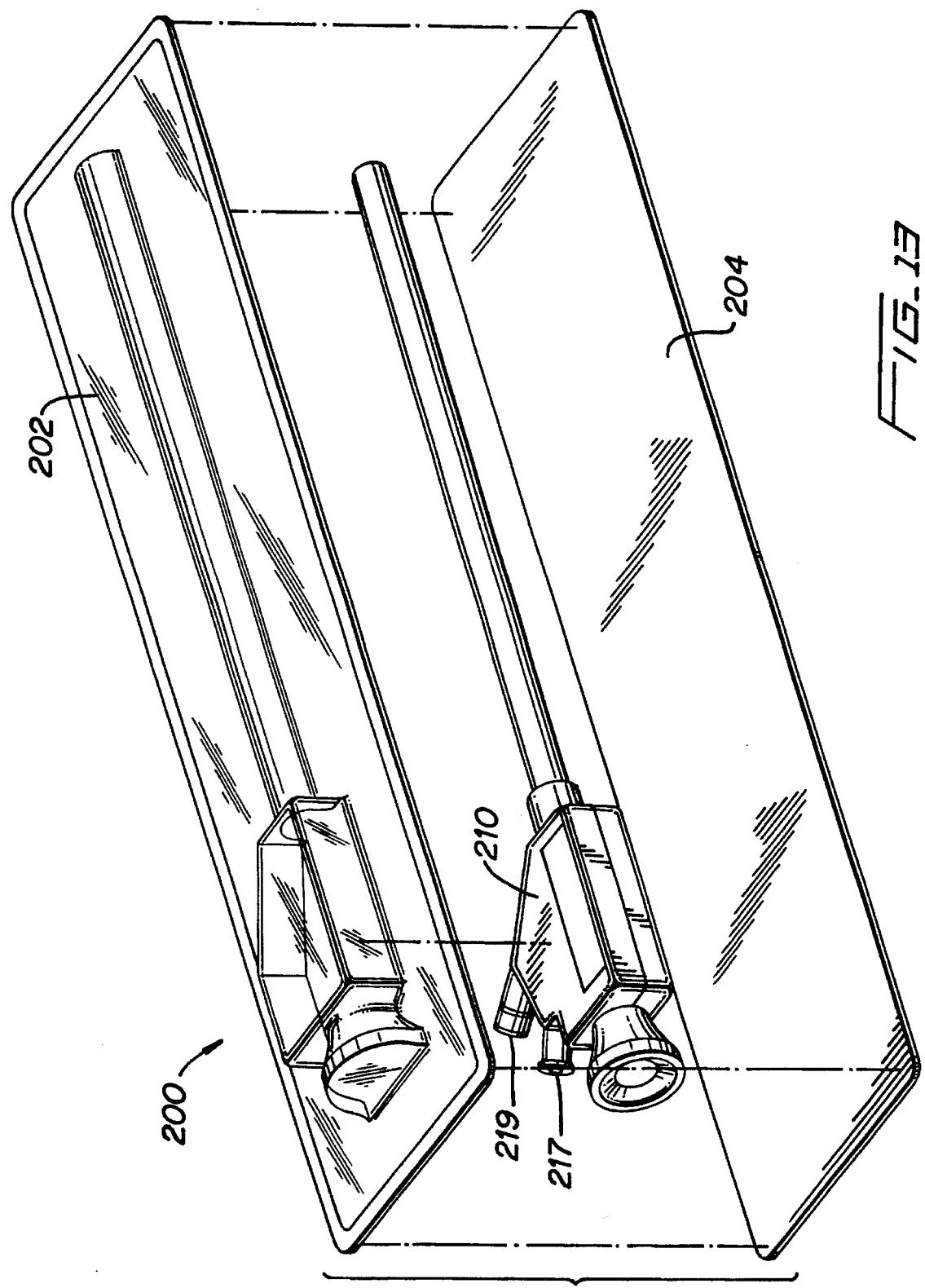
FIG. 13 is an exploded perspective view of an endoscope packaged in a molded-type blister pack.

By way of example only, referring to FIG. 13, the endoscope 212 having a distal lens surface coated with polyHEMA may be packaged in a molded plastic package member 202 with a bacteria barrier lid 204 adhered thereto around the periphery of the package. Thereafter, the packaged endoscope may be sterilized in a standard gas or radiation sterilization cycle and furnished to the user in a sterile condition. The endoscope could also be furnished to the user in a non-sterile condition for sterilization by the user.

As shown in FIG. 13, endoscope 212 includes a light cable connection 217 for connection to an illumination source to supply illumination to the endoscope in a known manner. Endoscope 212 also includes a fluid connection port 219 for connection to a source of antifogging solution. Fluid port 219 communicates with any of the internal endoscope conduits previously described for conveying the antifogging solution to the distal lens surface.

Endoscopes having features other than the particular features depicted are also contemplated. For example, an endoscope image transmission system may include a fiber optic bundle, relay rods or lenses, or a solid state sensor, such as a CCD, to transmit the image from the objective lens system to the eyepiece viewing lens system (not shown in the drawings) located at the proximal end of the endoscope. A camera adapter may be provided at the proximal end of the endoscope to permit the image to be displayed on a television/video monitor. The endoscope insertion member may also include tube channels which allow for passage of biopsy and fulguration instruments, laser beam devices, catheters, or instruments for contacting the distal objective lens with the antifogging composition. A power source for driving the endoscope aspiration, gas insufflation, and liquid instillation operations may also be included. Accordingly, one with skill in the art may make modifications to the endoscope and methods which are intended to be covered by the following claims.

What is claimed is:

1. A method for eliminating fogging of an endoscope lens which comprises:

introducing a distal end portion of an endoscope into a body;

passing a fluid composition comprising polyalkylene oxide through a conduit in the endoscope; and contacting a lens associated with said distal end portion of said endoscope with the composition comprising polyoxyalkylene which has been passed through the conduit while said lens remains within the body.

2. The method according to claim 1, wherein said polyoxyalkylene is selected from the group consisting of homopolymers, copolymers and blends of polypropylene oxide and polyethylene oxide.

3. The method according to claim 1, wherein said polyoxyalkylene comprises a polyoxypropylene-polyoxyethylene block copolymer.

4. The method according to claim 3, wherein said polyoxypropylene-polyoxyethylene block copolymer has a molecular weight of from about 8,000 to about 13,000.

5. The method according to claim 1, wherein said polyoxyalkylene is present in an amount of about 0.01 to about 5 weight percent of said composition.

6. The method according to claim 1, wherein said composition further comprises a biocompatible solvent selected from the group consisting of water and saline solution.

7. A surgical apparatus comprising:

a) an endoscope having an elongated insertion member;

b) at least one lens disposed adjacent a distal end of said member;

c) a reservoir containing an antifogging solution comprising polyalkylene oxide, said reservoir being operatively associated with said member; and d) means for selectively directing a quantity of said solution comprising polyalkylene oxide from said reservoir to said at least one lens while said distal end of said endoscope is positioned within a body.

8. The surgical apparatus as recited in claim 7, wherein said reservoir is disposed within said elongated insertion member.

9. The surgical apparatus as recited in claim 7, wherein said directing means further comprises an outlet for directing a spray of said solution toward said at least one lens, said outlet being movable from a first position within said elongated insertion member to a second extended position distal said lens.

10. A surgical apparatus comprising:

an endoscope having a distal end and a proximal end and a lens disposed at said distal end having an exposed distal surface, said distal lens surface being coated with a composition comprising polyHEMA; and a conduit for conveying fluid from said proximal end to said distal end and directing said fluid onto at least a portion of said distal lens surface.

11. The surgical apparatus according to claim 10 wherein said fluid is water.

12. The surgical apparatus according to claim 10 wherein said fluid is saline solution.

13. The surgical apparatus according to claim 10 wherein said conduit has an outlet end movable from a first position not extending beyond the distal end of said endoscope to a second position extending beyond the distal end of said endoscope.

14. The surgical apparatus according to claim 10 wherein said endoscope is contained in a sterile package.

15. A method of preventing fogging of an endoscope comprising:

coating the distal lens of an endoscope with a solution of polyHEMA;

drying the solution to form a polyHEMA coating on the distal lens;

inserting the endoscope into a mammalian body;

applying antifogging solution to the distal lens surface through a fluid conduit on the endoscope.

16. The method of claim 15 wherein said step of coating the distal lens with a solution of polyHEMA comprises coating the distal lens with a solution of from about 0.1 to about 25 percent polyHEMA.

17. The method of claim 15 wherein said step of coating the distal lens with a solution of polyHEMA comprises coating the distal lens with a solution of from about 1 to about 5 percent polyHEMA.

18. The method of claim 15 wherein said step of coating the distal lens with a solution of polyHEMA comprise coating the distal lens with a solution of from about 2 to about 3 percent polyHEMA.

19. The method of claim 15 wherein said step of coating the distal lens with a solution of polyHEMA comprises coating the distal lens with polyHEMA in ethanol.

20. The method of claim 15 wherein said step of applying an antifogging solution to the distal lens surface comprises applying an antifogging solution selected from the group consisting of water, saline and polyoxyalkylene.

21. The method of claim 15 further comprising the following steps after said drying step and prior to said inserting step:

packaging said endoscope with the polyHEMA coating on the distal lens surface in a package;

sterilizing said packaged endoscope; and removing said packaged sterile endoscope from the package.

22. The method of claim 15 further comprising the following steps after said drying step and prior to said inserting step:

sterilizing said endoscope with said polyHEMA coating on said distal lens surface.

* * * * *